United States Patent [19]
Goswami et al.

[11] Patent Number: 5,997,907
[45] Date of Patent: Dec. 7, 1999

[54] ENHANCEMENT OF GUAR SOLUTION STABILITY

[75] Inventors: Animesh Goswami, Plainsboro; Paul-Joel Derian, Lawrenceville, both of N.J.

[73] Assignee: Rhodia Inc., Cranbury, N.J.

[21] Appl. No.: 08/994,410

[22] Filed: Dec. 19, 1997

Related U.S. Application Data

[60] Provisional application No. 60/040,182, Mar. 12, 1997.

[51] Int. Cl.$^6$ .............................. A61K 9/50; A61K 7/00; A61K 9/14; A61K 47/00
[52] U.S. Cl. ..................... 424/500; 424/401; 424/485; 424/499; 514/780; 514/782
[58] Field of Search .................................. 514/780, 782; 424/401, 499, 500, 485

[56] References Cited

U.S. PATENT DOCUMENTS 5,622,693   4/1997   Funatsu ..................................... 424/69

FOREIGN PATENT DOCUMENTS

| | | |
|---|---|---|
| 0 122 528 | 1/1984 | European Pat. Off. . |
| 263 449 A1 | 8/1987 | Germany . |
| 2-242641 | 9/1990 | Japan . |
| 4-218371 | 8/1992 | Japan . |
| 5-276911 | 10/1993 | Japan . |
| 93/08704 | 5/1993 | WIPO . |
| 96/28458 | 9/1996 | WIPO . |

OTHER PUBLICATIONS

"Hawley's Condensed Chemical Dictionary", revised by R.J.Lewis, Sr., Van Nostrand Reinhold, pp. 89 and 555, 1997.

Deeble et al., "The treatment of aqueous gum arabic solutions with ultraviolet radiation", Food Hydrocolloids, vol. 4, No. 4, pp. 313–321, 1990.

Systems to Prevent Loss of Functionality on Heat Treatment of Galactomannans, Jr. R. Mitchell, J. Reed, S. E. Hill and E. Rogers, Dept. of Applied Biochemistry and Food Science, University of Nottingham, Sutton Bonington, Loughborough, Leic LE12 5RD, UK pp. 141–143.

Biopolymer Solution Viscosity Stabilization Polymer Degradation and Antioxidant Use, Scott L. Wellington, SPE, Shell Development Co., Society of Petroleum Engineers Journal, Dec. 1983, pp. 901–912.

Untersuchungen uber Mikroorganismen in Verdickungsmitteln, Keimzahlen aerober Mikroorganismen, P. Souw and H. J. Rehm, Institut for Mikrobiologie der Universitat Münster, Dec. 27, 1972, pp. 187–192.

Microorganisms in Gums, V. Degration of the Galactomannans Guar Gum and Locust Bean Gum by Different Bacilli, P. Souw and H.J. Rehm, Institute of Microbiology, University of Münster, Germany, pp. 47–58.

*Primary Examiner*—Shelley A. Dodson
*Assistant Examiner*—Marina Lamm
*Attorney, Agent, or Firm*—Andrew M. Solomon

[57] ABSTRACT

Methods for enhancing the stability of thickening agent solutions, especially guar solutions, by sterilizing the solution with UV light and/or adding a surfactant to the solution are disclosed. Thickening agent solutions and powders, including guar solutions and powders, as well as products made from these solutions and powders, are also disclosed.

5 Claims, 3 Drawing Sheets

ENHANCEMENT OF GUAR SOLUTION STABILITY

This application claims the benefit of U.S. provisional application Ser. No. 60/040,182 filed Mar. 12. 1997.

BACKGROUND OF THE INVENTION

1. Field of the Invention

The present invention relates to enhancing the stability of thickening agent solutions, including but not limited to guar solutions. More specifically, the present invention relates to enhancing the stability of thickening agent solutions by sterilizing these solutions with UV light, and/or by adding a surfactant to these solutions.

2. Background Information

Natural and synthetic polymers containing hydroxy groups have been used as thickeners for foods, coatings, paints, explosive slurries, oil well fluids, cosmetics and other personal care products, and many other functional applications.

One class of polymers that have been widely used as suspending and viscosity agents are polygalactomannans. Polygalactomannans are polysaccharides composed principally of galactose and mannose units and are usually found in the endosperm of leguminous seeds such as guar, locust bean, honey locust, flame tree, tara, fenugreek and the like. Guar flour, for example, is composed mostly of a galactomannan which is essentially a straight chain mannan with single membered galactose branches. The mannose units are linked in a 1-4-$\beta$-glycosidic linkage and the galactose branching takes place by means of a 1–6 linkage on mannose units in an irregular manner. The ratio of galactose to mannose in the guar polymer is about one to two.

Locust bean gum is also a polygalactomannan gum of similar molecular structure in which the ratio of galactose to mannose is one to four. Guar and locust bean gum are the preferred sources of the polygalactomannans, principally because of the commercial availability thereof.

Polygalactomannan may be used in either its natural state (i.e., pure guar gum or locust bean gum) or may be derivatized. Derivatized polygalactomannans include one or more non-ionic and/or ionic groups. Examples of such polygalactomannans include hydroxypropyl guar, hydroxyethyl guar, carboxymethyl guar, carboxymethyl hydroxypropyl guar and the like having varying degrees of substitution and molar substitution. Such derivatized polygalactomannans are sold by Rhône-Poulenc Inc. under the trade names Jaguar 8000 (hydroxypropyl guar), Jaguar 8710 (carboxymethyl guar) and Jaguar 8600 (carboxymethyl hydroxypropyl guar). Many commercially available starting guar materials may contain small amounts of additives such as borax, glyoxal and the like. These starting materials are expressly covered as constituting part of the present invention.

The term "degree of substitution" as employed herein is the average substitution of functional groups per anhydro sugar unit in the polygalactomannan gums. In guar gum, the basic unit of the polymer consists of two mannose units with a glycosidic linkage and a galactose unit attached to a hydroxyl group of one of the mannose units. On the average, each of the anhydro sugar units contains three available hydroxyl sites. A degree of substitution of three would mean that all of the available hydroxyl sites have been esterified with functional groups. A particularly preferred functional group is the carboxymethyl group, with good results obtained with starting materials having a degree of substitution of between about 0.0 and about 3.0, specifically including materials having a degree of substitution ranging from about 0.10 to about 0.15.

Similarly, the term "molar substitution" as employed herein is the average number of moles of functional groups per anhydro sugar unit in the polygalactomannan gum. A particularly preferred functional group is the hydroxypropyl group, with good results obtained with starting materials having a molar substitution of between about 0.0 and about 3.0. In a preferred embodiment, the resulting polysaccharide is carboxymethyl hydroxypropyl guar having a molar substitution of hydroxypropyl groups of between about 0.25 and about 0.35 and a degree of substitution of carboxymethyl groups of between about 0.10 and about 0.15.

While the use of polygalactomannans, and guar gum in particular, as thickening agents has been met with great success, it is still desired to improve the physical properties of the guar gum when dispersed in a solution such as water. One such property is guar's ability to retain its viscosity over extended periods. Solutions of guar in water are known to lose viscosity over time.

As will be known to those skilled in the art, the guar endosperm is commonly referred to as "purified splits", "double purified splits" or "triple purified splits" depending upon the degree of purification. "Purified splits" are obtained by mechanical separation of the endosperm from the hull and germ of the guar seed in as pure and intact a form as possible with no other processing steps. Repeating the process produces double purified splits. Repeating the process again produces triple purified splits. Splits are then ground into guar powder.

There are several methods to sterilize solutions including, for example, steam sterilization, pasteurization, and chemical sterilization. Steam sterilization of guar solutions results in polymer degradation and loss of viscosity of the guar solution; this reduction in viscosity can be as high as 80%. Pasteurization can be similarly ineffective in that certain spore forming bacteria such as Bacillus species, which have been found in guar, usually cannot be killed by simple pasteurization processes; pasteurization can even facilitate spore germination. Chemical sterilization such as the use of biocides and bactericides as well as chemicals such as ethylene oxide also have drawbacks. Use of various biocides and/or preservatives is often restricted or even prohibited with certain products such as food products and personal care products. Use of ethylene oxide can lead to formation of trace amounts of ethylene glycol and 2-chloroethanol on guar.

Wellington, *Soc. Pet. Eng. J.*, 23:901–912 (1983) and Mitchell, et al., *Food Hydrocolloids*, 5:141–143 (1991) report the use of antioxidants to stabilize various galactomannans such as xanthan gum and guar gum. Neither of these references report the use of UV light sterilization or the use of surfactants, alone or in combination, to increase the stability of thickening agent solutions.

The use of ultraviolet (UV) radiation for sterilization of various products is known. Many industrial systems are available for UV sterilization, especially for sterilization of water. For example, laboratory water purification systems such as the Milli-Q UV Plus Water System, commercially available from the Milli-Pore Corporation, uses UV light to sterilize water. The use of UV light to sterilize guar solutions or other thickening agents, however, has not been reported.

Thus, improved methods for sterilizing or otherwise treating guar solutions so they retain their viscosity stability over time are needed.

The entire disclosure of U.S. provisional application Ser. No. 60/040,182, filed Mar. 12, 1997, is considered as being part of this disclosure and is hereby incorporated by reference herein.

SUMMARY OF THE INVENTION

The present invention has met the above described needs by providing methods for producing thickening agent solutions, especially guar solutions, with increased or enhanced stability. In one embodiment, the methods for enhancing stability of guar solutions generally including sterilizing the guar solution with UV light. The methods of another embodiment generally include adding a surfactant to the guar solution. In another embodiment, guar solutions are treated both by sterilization with UV light and addition of a surfactant. The enhanced stability is greater when these methods are used together than when either method is used alone, although each method alone yields enhanced stability as well.

The present invention also provides thickening agent solutions having enhanced stability, which have prepared by sterilization of a thickening agent solution with UV light, and/or addition of a surfactant to the thickening agent solution. The thickening agent solutions prepared according to the methods of the present invention have enhanced stability and therefore enhanced shelf-life; products incorporating these thickening agent solutions will also have enhanced shelf-life. The present invention also provides thickening agent powders having enhanced stability. These powders are prepared by dehydrating the thickening agent solutions prepared as described herein.

It is therefore an object of the present invention to provide guar solutions that retain their viscosity stability over time.

Another object of the invention is to provide thickening agent solutions that retain their viscosity stability over time.

Another object of the invention is to provide guar solutions having enhanced stability when compared with guar solutions made by methods currently known in the art.

A further object of this invention is to provide guar solutions which can be used as thickening agents in various food products and personal care products.

Another object of the present invention is to provide a method for enhancing the stability of guar solutions by sterilizing the solutions with UV light.

Another object of the present invention is to provide a method for enhancing the stability of guar solutions by adding a surfactant to the solutions.

Yet another object of the present invention is to provide a method for enhancing the stability of guar solutions by sterilizing the solutions with UV light and adding surfactant to the solutions.

A further object of the invention is to provide a method for enhancing the stability of thickening agent solutions subject to microorganism contamination by sterilizing the solutions with UV light and/or adding surfactant to the solutions.

Another object of this invention is to provide a method for sterilizing thickening agent solutions subject to microorganism contamination by exposing the solutions to UV light and/or adding surfactant to the solutions.

Another object of the present invention is to provide thickening agent powders having enhanced stability.

These and other objects of the invention will be readily apparent to those skilled in the art from the following description.

DETAILED DESCRIPTION OF THE INVENTION

Figure 1:
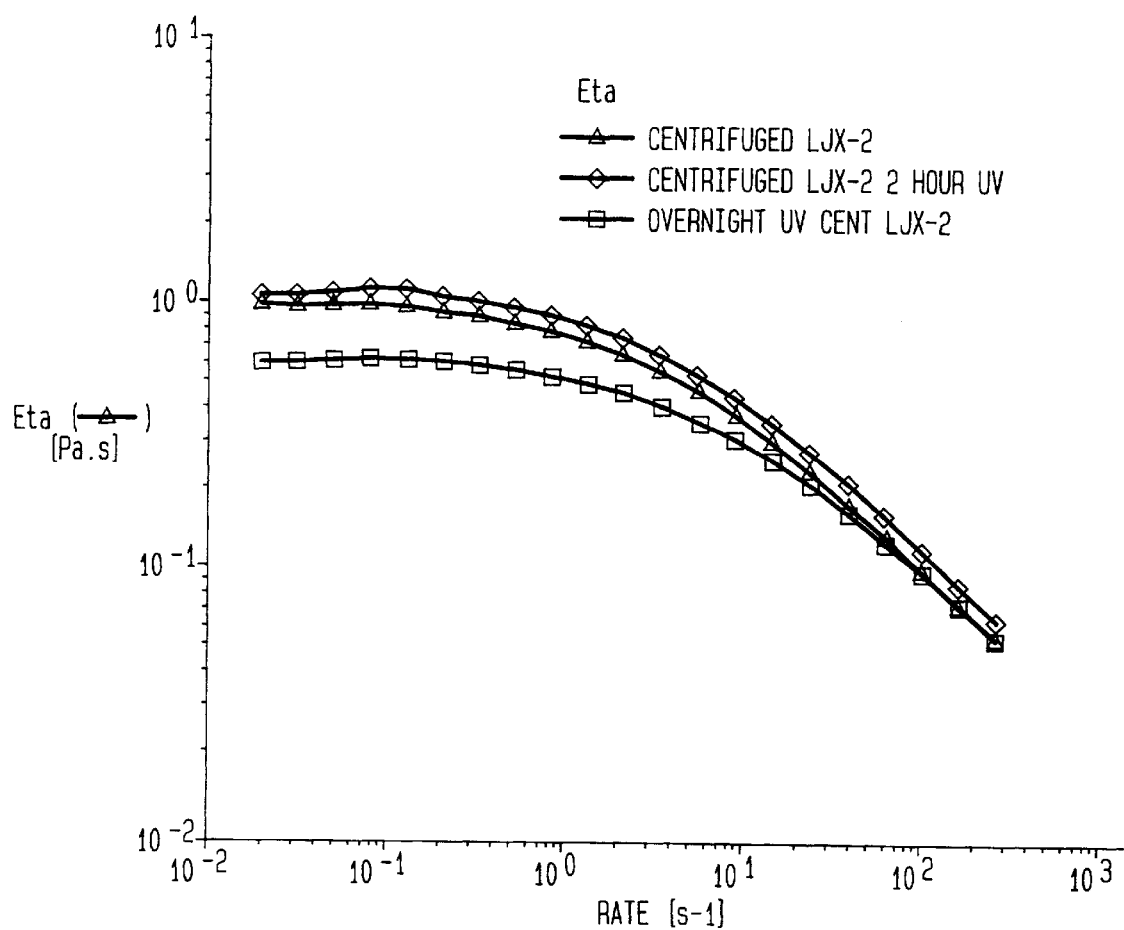
FIG. 1 shows the viscosity of guar solutions both before and after UV exposure, determined according to the methods of Example II.

The present invention is directed to a method for sterilizing a thickening agent solution by exposing the solution to UV light. One effect of this sterilization is improving the viscosity of the solution. Thus, the present invention is further directed to a method for enhancing the stability of a thickening agent solution comprising sterilizing the solution with UV light. The term "thickening agent" as used herein refers to any compound used to increase the viscosity of liquid mixtures and solutions and to aid in maintaining the stability of these liquids through emulsification. Any thickening agent solution subject to degradation and loss of viscosity due to microorganism contamination can be treated according to the methods of the present invention. Such thickening agents include but are not limited to polysaccharides such as galactomannans. Guar solutions are preferred. While guar solutions are primarily disclosed herein as the preferred thickening agent of the present invention, it is to be understood that any thickening agents as described above are within the scope of the present invention.

"Guar" as used herein refers to any guar or guar derivative including but not limited to food grade and industrial grade guars and guar derivatives, purified splits, double purified splits and triple purified splits.

The microorganisms present in guar powders and guar splits ("inherent microorganisms") have been identified as belonging to the genus Bacillus. The inherent microorganisms are believed to be responsible for the fast degradation of guar and the viscosity loss of guar solutions. The reductions in viscosities of various guar solutions are directly related to the quantity of inherent microorganisms present in them. Bacillus species degrade guar to low molecular weight polysaccharides in a relatively short period of time. Other microorganisms generally present in the atmosphere ("atmospheric microorganisms") which can contaminate guar are less adapted to degrading guar, and reduce the viscosity of guar solutions at a slower rate. Molecular weight data obtained from gel permeation chromatography ("GPC") has also been used to follow degradation.

Guar solutions are stable over a wide pH range. The stability is drastically reduced under only highly acidic (pH 2) and highly basic (pH 12) conditions. At pH 2, viscosity decreases with time and only about 3% of initial viscosity is retained after about one month. Guar solutions retain a slightly higher percent of their initial viscosity (about 20%) at pH 12 after about one month. The reason for the sharp initial drop of viscosity at pH 12 has not been identified, although it has been determined that the drop is not due to depolymerization since the molecular weight as measured by GPC does not show any appreciable change. One hypothesis is that the guar molecules are "hyperentangled" with many junction zones in solution; the individual polymer chains quickly separate from one another along these junction zones under basic conditions thereby causing a drop of viscosity. The inventors do not wish to be bound by this mechanism, however.

Any source of UV light can be used in the sterilization methods of the present invention. UV lights are available, for example, from Philips, Thomas Scientific and Wilmad Glass. Similarly, a variety of configurations can be used, such as placing the UV light above the solution, placing the UV light at one or more points around the solution, or flowing the solution through the path of UV light. The entire spectrum of UV light can be used, as can a smaller range of wave lengths. The most preferred wavelength is about 254 nanometers (nm), which is recognized by those skilled in the art to have the greatest germicidal effect. Ultraviolet radiation works by photochemical transformation of the pyrimidine bases cytosine and thymine of the microorganism DNA. Since sterilization with UV light does not result in the thickening agent solution having retained biocidal activity, this method is especially well suited for use with food and personal care products in which biocide use is restricted or prohibited.

The thickening agent solution should be exposed to UV light under conditions sufficient to impart the desired amount of sterilization to the solution, while retaining all or nearly all of the initial viscosity of the solution. The exposure time of the solution to the UV light source necessary to effect this sterilization will vary depending on various parameters. Some experimental parameters which should be considered include, but are not limited to, solution concentration, clarity of solution, height of solution, open surface area of the solution, intensity of the source, distance of solution from the source, the transmittance of the medium at the germicidal wavelength, and the like. The type and amount of bacterial contamination is also very important. Bacterial spores are known to be more resistant to the UV radiation than the vegetative cells. Thus, a solution containing fewer spores will be relatively easier to sterilize by UV light. Before UV exposure, heating the solution is beneficial to germinate the spores and increase the efficiency of sterilization. It is possible to control these various factors to determine the best UV light conditions needed to effect the desired level of sterilization for a given solution. Determining this desired level is well within the skill of one practicing in the art. Efficacy of sterilization under various conditions can be confirmed by plating the solution on agar and checking for microorganism growth. A two hour exposure time, with the light source about 60 cm from the solution, is optimum for sterilizing a 0.5% guar solution with no change in viscosity. Long exposure times (about 20 hours), such as overnight exposure to UV radiation, at 60 cm distance and a concentration of 0.5% can be too much, however, and can actually result in reduction in viscosity. Cooling the solution during UV exposure may be beneficial to disperse the heat.

The present invention is also directed to a method for sterilizing a thickening agent solution by adding surfactant to the solution.

The present invention is also directed to a method for enhancing the stability of thickening agent solutions comprising adding an effective amount of surfactant to the solutions. Again, the preferred thickening agent is guar, although any other thickening agents as described above are within the scope of the invention.

Any suitable surfactant can be used so long as compatibility problems do not arise. As will be appreciated by one skilled in the art, the suitability of various surfactants will vary depending on the end use of the thickening agent solution. For example, the use of some surfactants in food or personal care products may be restricted or prohibited. As used herein, and as will be appreciated by one skilled in the art, a "surfactant" is a compound having both hydrophobic and hydrophilic surface-active moieties. Anionic, cationic, nonionic and amphoteric surfactants can all be used. Examples of suitable anionic surfactants include, but are not limited to, sulfonates, sulfates, phosphates, and succinates; sodium and potassium salts of these surfactants are preferred because of their greater solubility in water. Examples of suitable cationic surfactants include but are not limited to ammnonium bromides; nonionic surfactants include but are not limited to alkyl ethoxylates, alkyl gluccosides and alkyl phenol ethoxylates; and amphoteric surfactants include but are not limited to betaines, amphoacetates, and amphodiacetates. A preferred anionic surfactant is sodium dodecyl sulfate (SDS) and a preferred cationic surfactant is dodecyl trimethyl ammonium bromide; SDS is most preferred for the methods of the present invention.

The mechanism by which SDS and other surfactants stabilize guar solutions is not certain. SDS is known to be a strong enzyme denaturing agent, and therefore may function by denaturing the enzymes produced by the microbes present in guar; the inventors do not wish to be bound by this mechanism, however.

The term "effective amount" as used herein refers to that amount of surfactant needed to impart the desired level of stability to guar solutions. This amount will vary depending on various factors such as the type of surfactant, the concentration of the surfactant and the end use of the guar solution. Generally, the surfactant concentration will range between about 0.001 M and about 10 M, with a concentration of about 0.1 M being preferred.

The present invention is further directed to a method for enhancing the stability of thickening agent solutions by both sterilizing the solution with UV light and adding a surfactant to the solution. The surfactant can be added to the solution either before or after the sterilization with UV light. Use of both UV sterilization and surfactant addition will result in greater enhanced stability than the use of surfactant or UV light alone.

Another embodiment of the present invention provides thickening agent solutions, preferably guar solutions, having enhanced stability. These solutions are generally prepared by treating conventionally prepared solutions by sterilizing the solutions with UV light and/or adding a surfactant to the solutions. For example, such guar solutions are prepared by dissolving guar powder in deionized water using continuous agitation. This embodiment of the present invention encompasses guar and guar derivative solutions of any concentration and includes the use of industrial grade and food grade guars, purified splits, double purified splits and triple purified splits. Thus, industrial and food grade guar solutions having enhanced stability are provided. Other thickening agent solutions having enhanced viscosity stability are also provided.

Because of these above properties, the thickening agent solutions of the present invention are suitable for a wide range of commercial applications, including but not limited to: compounds used in oil and gas recovery; personal care products; textile chemicals; dyes; paper chemicals including print and processing chemicals; paints; food products; pharmaceutical products; explosives; absorbent materials; agricultural products; cosmetics; and any other application where enhanced stability would be beneficial. Accordingly, such products containing the novel thickening agent solutions of the present invention are also within the scope of this invention. Preferred are those products containing one or more of the guar solutions prepared as described herein.

Yet another embodiment of the present invention provides thickening agent powders, preferably guar powders, having enhanced stability. These powders will have been treated according to the methods of the present invention. That is, thickening agent solutions are prepared and treated by sterilization with UV light and/or addition of a surfactant. These solutions, as discussed above, show an enhanced viscosity stability. Dehydration of these solutions, such as through standard evaporation methods known in the art, yields dry thickening agent powders. These powders, in turn, can be dissolved again in water or other solvents to produce a thickening agent solution having long-term stability.

EXAMPLES

The following examples are intended to illustrate the invention and should not be construed as limiting the invention in any way.

Example I
Preparation of Guar Solution

The guar solution utilized in the examples was made from guar LJX-2, Lot 9504551 made in India and available from Rhone-Poulenc Inc., Cranbury, N.J. About 15 g of the guar were mixed with deionized water (3 liters) using an overhead stirrer. The mixture was gently stirred at room temperature (about 20–22° C.) overnight. A portion of this 0.5% guar solution was centrifuged at about 22° C. at 20000 g for about 2 hours. The centrifuged guar solution at the top was separated from the insoluble material at the bottom.

Example II
UV Sterilization of Guar Solution

The centrifuged guar solution prepared according to Example I was heated at about 90° C. for about 15 minutes and subsequently cooled back to room temperature. The guar solution (about 800 ml) was then placed in two open beakers (1 liter). The approximate solution height was about 10 cm in each beaker. The beakers were kept in a microbiological hood (Nuaire, Model NU-425-600) fitted with a UV light (Philips, Sterilamp G36T6L) approximately 60 cm vertical distance from the lamp. The UV light was turned on. One solution was exposed to UV light for 2 hours while the other was exposed to UV light overnight, about 20 hours. The viscosity of the two solutions exposed to UV light, as well as a centrifuged guar solution not exposed to UV light was determined; results are presented in FIG. 1. The viscosity of the 2 hour UV exposed solution was almost the same as that of the centrifuged guar solution not exposed to UV light. Overnight exposure to UV light actually reduced the viscosity by about 40%. Viscosity was determined throughout these examples by an ARES Rheometer, available from Rheometric Scientific.

Example III
UV Sterilization of Guar Solution

A second 0.5% guar solution was prepared by mixing 5 g of guar in 1 liter of deionized water and heating at 90° C. for 30 minutes. This solution (without centrifugation) was also sterilized by 2 hour UV exposure; no loss of viscosity was observed. Thus, the methods of the present invention apply to enhancing the stability of both centrifuged and non-centrifuged guar solutions.

Example IV
Microbiological Plate Count Test of Guar Powder

The microbiological populations of guar throughout the examples were assayed by the aerobic plate count method, which methods are standard in the art. Generally, in the method used here involved mixing the guar solution with an agar mix comprised of Trypticase Soy Agar (TSA), 1.5% Polysorbate 80 (such as Tween products available from Difco Labs, Detroit, Mich., or ICI United States) and sterile water. The guar/agar mix is then overlayed with a second layer of the agar mix and allowed to incubate for about four days. The plates are checked periodically for microorganism growth.

Example V
Microbiological Plate Count Test of Guar Solution of Examples I and II The plate count method as described in Example IV was done by plating 1 ml of the following different solutions: guar solution prepared according to Example I; centrifuged guar solution prepared according to Example I and further heat treated at 90° C. for 15 min; guar solutions treated with UV light for two hours prepared according to the methods of Example II; and guar solutions treated with UV light for twenty hours prepared according to the methods of Example II. The guar solution, and centrifuged guar solution and centrifuged heated guar solution showed significant number of spore forming microorganisms. The 2 hour and overnight UV exposed solutions showed no colonies, indicating the removal of inherent microorganisms by the UV exposure.

Example VI
Microbiological Plate Count Test of Guar Solution of Example III

The plate count method as described in Example IV was done using 1 ml of each of the guar solutions both before and after UV exposure prepared as described in Example III. The solution not subjected to UV exposure showed significant numbers of spore forming microorganisms. The solution exposed to UV light showed no colonies, indicating sterilization by UV exposure.

Example VII
Viscosity Loss of Sterilized and Non-Sterilized Solutions

The viscosity loss of the centrifuged guar solution prepared according to Example I (containing inherent enzymes and inherent microorganisms), centrifuged and heated guar solution prepared as described in Example II without UV sterilization (containing inherent microorganisms) and 2 hour UV sterilized solution prepared as described in Example II (free from inherent enzymes and microorganisms) were studied.

The centrifuged guar solution, centrifuged and heated guar solution and 2 hour UV treated guar solution were kept under ambient conditions. The solutions were covered with PVC wrap to prevent evaporation. No special recautions were taken to maintain sterility in this experiment.

Figure 2:
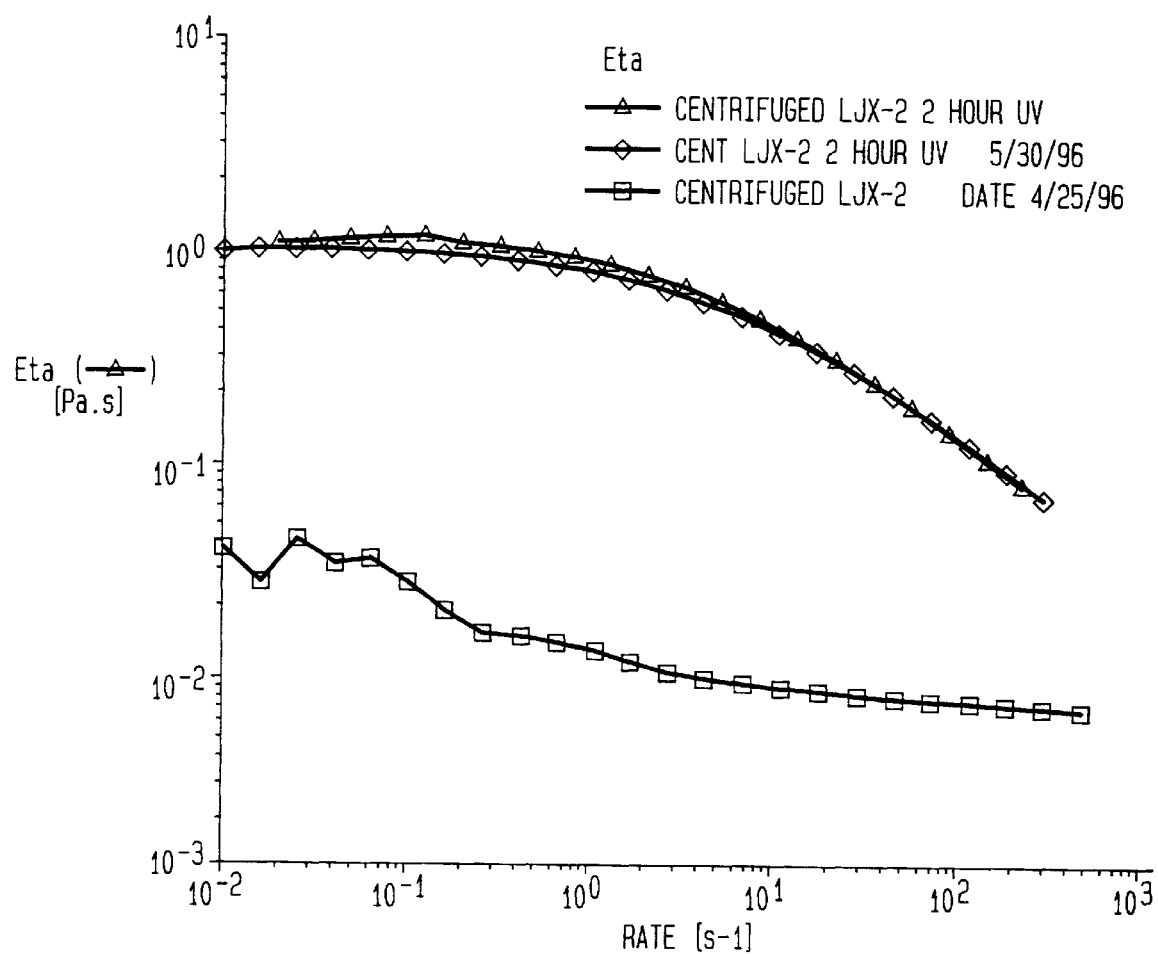
FIG. 2 shows the comparison of viscosity of non-sterilized and sterilized guar solutions over two months, determined according to the methods of Example VII.

Samples were withdrawn at various times. Rheological studies were done using an ARES Rheometer. Steady rate sweep test was performed using a double walled couette. The viscosity (Eta) values were plotted versus shear rate as shown in FIG. 2. The zero shear viscosities of different solutions can be used for comparison. The initial viscosity of the centrifuged guar solution subjected to a 2 hour UV exposure is marked by triangles ($\Delta$). The viscosity of this UV sterilized guar solution after about 2 months is marked by diamonds ($\Diamond$). The viscosity of the centrifuged guar solution not subjected to UV exposure after about 1 month is marked by squares ($\square$). As can be seen in FIG. 2, the viscosity of the non-sterilized guar solutions dropped considerably from the initial reading in approximately one month. Indeed, the viscosity of the non-sterilized guar solution became like solvent water after one month. The viscosity of the UV sterilized guar solution, however, remained fairly constant after two months. This illustrates that viscosity of the solutions can be retained over a long time by the use of UV sterilization.

In another experiment the guar solutions as described above were kept under aseptic condition in the microbiological hood to prevent the growth of atmospheric microorganisms. Both the centrifuged and centrifuged and heated solutions (containing the inherent microorganisms) lost viscosity over time and had the viscosity of solvent water in two weeks. The 2 hour UV exposed solution (free from the inherent microorganisms) retained the high viscosity levels determined at the start of the experiment.

In yet another embodiment, the viscosity of solutions made according to Example III was followed using a Brookfield Viscometer; the UV sterilized solution retained viscosity for a much longer period than the non-sterilized solution.

Example VIII
Long Term Stability of UV Sterilized Guar Solution

Figure 3:
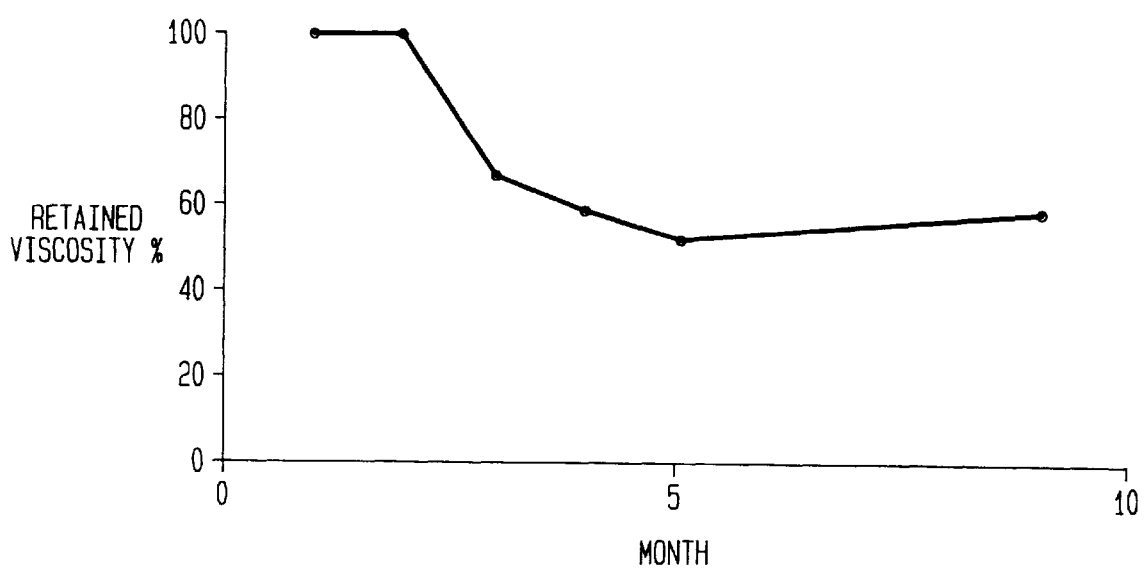
FIG. 3 shows the long term stability of a UV sterilized guar solution over about 9 months, determined according to the methods of Example VIII.

The long term stability of the guar solution sterilized with UV light for two hours prepared according to Example II was determined over a period of about 9 months. During this period the guar solution was stored on a regular laboratory bench covered with a PVC wrap to prevent evaporation and samples were occasionally removed from the beaker. No special precautions were taken to maintain sterility. The viscosity was measured as described above. Results are shown in FIG. 3. As can be seen from the figure, viscosity was still about 50% after about 9 months. The long term drop in viscosity is believed to be due to contamination by other atmospheric microorganisms. Thus, maintaining more sterile conditions would yield a prolonged, higher level of viscosity.

Example IX
Effect of Surfactant on the Stability of Guar Solution

The effect of surfactants on the viscosity of a 0.2% guar solution was determined as outlined in Table I below. CSA 200/50 guar, available from Rhône-Poulenc, was used in this example. The solution was prepared by dissolving about 0.2 g of the guar in 1 liter of sterile water. Viscosity was determined as described above.

TABLE 1

| Surfactant | Surfactant Concentration | Retained Viscosity (%) |
|---|---|---|
| Control | — | 65 |
| Dodecyl trimethyl ammonium bromide | 0.1M | 82 |
| Sodium dodecyl sulfate | 0.1M | 96 |

A control using no surfactant was run, as were two different surfactants. Retained viscosity, expressed in percent, was determined after twelve days according to the formula: 100× Viscosity at Day 12/Initial Viscosity. These results clearly showed that the stability of viscosity of the guar solution was enhanced by the use of surfactants.

What is claimed is:

1. A method for sterilizing or enhancing the stability of a guar gum solution comprising adding a surfactant selected from the group consisting of sulfonates sulfates, phosphates, succinates, ammonium bromides, alkyl ethoxylates, alkyl glucosides, alkyl phenol ethoxylated, betaines, amphoacetated and amphodiacetates and mixtures thereof to said solution.

2. A method for sterilizing or enhancing the stability of a guar gum solution comprising:
   a) sterilizing said solution by exposure to UV light; and
   b) adding a surfactant selected fromn the group consisting of sulfonates, sulfates, phosphates, succinates, ammonium bromides, alkyl ethoxylates, alkyl glucosides, alkyl phenol ethoxylates, betaines, amphoacetates and amphodiscetates and mixtures thereof either before or after sterilizing said solution.

3. A guar gum solution prepared by:
   a) forming a solution with said guar gum and water; and
   b) treating the solution of step a) with addition of an effective amount of surfactant selected from the group consisting of sulfonates, sulfates, phosphates, succinates, ammonium bromides, alkyl ethoxylates, alkyl glucosides, alkyl phenol ethoxylates, betaines, amphoacetates and amphodiacetates and mixtures thereof.

4. An oil field chemical, personal care chemical, cosmetic, textile chemical, dye, absorbent material, food product, pharmaceutical product, explosive, agricultural product, paper chemical or coating composition including a guar solution having enhanced stability prepared by:
   a) mixing guar powder in water with adequate stirring to disperse said guar powder; and
   b) treating the mixture of step a) with addition of an effective amount of surfactant selected from the group consisting of sulfanates, sulfates, phosphates, succinates, amnmonium bromnides, alkyl ethoxylates, alkyl glucosides, alkyl phenol ethoxylates, betaines, amphoacetates and amphodiacetates and mixtures thereof.

5. A guar gum powder prepared by:
   a) forming a solution with said guar gum and water;
   b) treating the solution of step a) with addition of an effective amount of surfactant selected from the group consisting of sulfanates, sulfates, phosphates, succinates, ammonium bromides, alkyl ethoxylates, alkyl glucosides, alkyl phenol ethoxylates, betaines, amphoacetates and amphodiacetates and mixtures thereof; and
   c) dehydrating the treated solution of step b) to form a guar gum powder.

* * * * *